(12) United States Patent
Sepetka et al.

(10) Patent No.: US 9,833,252 B2
(45) Date of Patent: *Dec. 5, 2017

(54) MULTI-COMPONENT OBSTRUCTION REMOVAL SYSTEM AND METHOD

(71) Applicant: MicroVention, Inc., Aliso Viejo, CA (US)

(72) Inventors: Ivan Sepetka, Los Altos, CA (US); Heath Bowman, Trabuco Canyon, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 211 days.

This patent is subject to a terminal disclaimer.

(21) Appl. No.: 14/207,331

(22) Filed: Mar. 12, 2014

(65) Prior Publication Data

US 2014/0277013 A1 Sep. 18, 2014

Related U.S. Application Data

(60) Provisional application No. 61/789,845, filed on Mar. 15, 2013.

(51) Int. Cl.
*A61B 17/221* (2006.01)
*A61B 17/3207* (2006.01)
(Continued)

(52) U.S. Cl.
CPC ........ *A61B 17/221* (2013.01); *A61B 17/3207* (2013.01); *A61B 17/32075* (2013.01);
(Continued)

(58) Field of Classification Search
CPC .............. A61B 17/22; A61B 17/22022; A61B 17/22031; A61B 17/221; A61B 2017/22034; A61B 2017/22035; A61B 2017/22081; A61B 2017/2212; A61B 2017/2215; A61B 18/1492; A61B 2018/0041; A61B 2018/00422;
(Continued)

(56) References Cited

U.S. PATENT DOCUMENTS 4,243,040 A * 1/1981 Beecher ........... A61B 17/22032
604/271
4,469,100 A * 9/1984 Hardwick ........ A61B 17/22032
604/908
(Continued)

FOREIGN PATENT DOCUMENTS

WO WO 2009/086482 A1 7/2009
WO WO 2012162437 A1 * 11/2012 ............... A61F 2/06

OTHER PUBLICATIONS

WIPO, U.S. International Search Authority, International Search Report and Written Opinion dated Jul. 11, 2014 in International Patent Application No. PCT/US2014/025032, 8 pages.

*Primary Examiner* — David C Eastwood
(74) *Attorney, Agent, or Firm* — Inskeep IP Group, Inc.

(57) ABSTRACT

An obstruction removal device is described having a retrieval component used to engage an obstruction within the vasculature and a sheath component that is capable of inverting to fold over the obstruction and the retrieval component. The sheath component helps contain the obstruction and minimizes trauma to the blood vessel during the removal process.

12 Claims, 15 Drawing Sheets

(51) Int. Cl.
*A61B 18/14* (2006.01)
*A61B 17/22* (2006.01)
*A61B 18/00* (2006.01)

(52) U.S. Cl.
CPC .............. *A61B 17/320725* (2013.01); *A61B 17/320758* (2013.01); *A61B 18/1492* (2013.01); *A61B 2017/2212* (2013.01); *A61B 2017/2215* (2013.01); *A61B 2017/22034* (2013.01); *A61B 2017/320716* (2013.01); *A61B 2017/320741* (2013.01); *A61B 2018/0041* (2013.01); *A61B 2018/00422* (2013.01); *A61B 2018/1435* (2013.01)

(58) Field of Classification Search
CPC ........ A61B 2018/1435; A61B 17/3207; A61B 17/32075; A61B 2017/320716; A61B 17/320725; A61B 2017/320741; A61B 17/320758
See application file for complete search history.

(56) References Cited

U.S. PATENT DOCUMENTS

| | | | |
|---|---|---|---|
| 5,908,435 A * | 6/1999 | Samuels | A61B 17/22031 606/127 |
| 6,001,118 A * | 12/1999 | Daniel | A61B 17/22031 606/159 |
| 6,039,721 A * | 3/2000 | Johnson | A61F 2/958 604/103 |
| 6,663,650 B2 | 12/2003 | Sepetka et al. | |
| 6,824,545 B2 | 11/2004 | Sepetka et al. | |
| 7,766,921 B2 * | 8/2010 | Sepetka | A61B 17/22031 606/127 |
| 7,780,696 B2 * | 8/2010 | Daniel | A61B 17/221 606/200 |
| 7,780,725 B2 * | 8/2010 | Haug | A61F 2/2418 623/2.17 |
| 8,100,935 B2 | 1/2012 | Rosenbluth et al. | |
| 8,252,017 B2 | 8/2012 | Paul, Jr. et al. | |
| 8,795,305 B2 | 8/2014 | Martin et al. | |
| 9,211,132 B2 * | 12/2015 | Bowman | A61B 17/22032 |
| 2002/0002383 A1 * | 1/2002 | Sepetka | A61B 17/22031 606/200 |
| 2002/0058964 A1 * | 5/2002 | Addis | A61B 17/1204 606/200 |
| 2002/0072764 A1 * | 6/2002 | Sepetka | A61B 17/22031 606/200 |
| 2002/0111646 A1 * | 8/2002 | Gifford, III | A61B 17/12022 606/195 |
| 2002/0123765 A1 * | 9/2002 | Sepetka | A61B 17/22031 606/192 |
| 2002/0138094 A1 * | 9/2002 | Borillo | A61F 2/013 606/200 |
| 2002/0169473 A1 * | 11/2002 | Sepetka | A61B 17/12022 606/200 |
| 2004/0073243 A1 * | 4/2004 | Sepetka | A61B 17/22031 606/159 |
| 2004/0098025 A1 * | 5/2004 | Sepetka | A61B 17/22031 606/200 |
| 2005/0033348 A1 * | 2/2005 | Sepetka | A61B 17/22031 606/200 |
| 2005/0216030 A1 * | 9/2005 | Sepetka | A61B 17/22031 606/113 |
| 2005/0216050 A1 * | 9/2005 | Sepetka | A61B 17/22031 606/200 |
| 2005/0288686 A1 * | 12/2005 | Sepetka | A61B 17/22031 606/113 |
| 2007/0038227 A1 | 2/2007 | Massicotte et al. | |
| 2008/0183197 A1 * | 7/2008 | Sepetka | A61B 17/22031 606/159 |
| 2010/0114017 A1 * | 5/2010 | Lenker | A61B 17/12118 604/96.01 |
| 2010/0249815 A1 * | 9/2010 | Jantzen | A61B 17/22031 606/159 |
| 2012/0041449 A1 * | 2/2012 | Eckhouse | A61B 17/221 606/127 |
| 2012/0089216 A1 * | 4/2012 | Rapaport | A61B 17/32072 623/1.11 |
| 2012/0143231 A1 * | 6/2012 | French | A61B 17/22031 606/159 |
| 2012/0310251 A1 | 12/2012 | Sepetka et al. | |
| 2012/0330350 A1 * | 12/2012 | Jones | A61B 17/221 606/200 |
| 2014/0005713 A1 * | 1/2014 | Bowman | A61B 17/22032 606/200 |
| 2014/0276403 A1 | 9/2014 | Follmer et al. | |

\* cited by examiner

MULTI-COMPONENT OBSTRUCTION REMOVAL SYSTEM AND METHOD

RELATED APPLICATIONS

This application claims priority to U.S. Provisional Application Ser. No. 61/789,845 filed Mar. 15, 2013 entitled Multi-Component Obstruction Removal System, which is hereby incorporated herein by reference in its entirety.

BACKGROUND OF THE INVENTION

The present invention relates to devices used to capture and remove obstructions, such as clots, foreign body matter or other matter, from the vascular system, and delivery of these devices to a target area within the vascular system.

The buildup of thrombus in vasculature can lead to formation of blood clots. The formation of clots can result in restricted blood supply to downstream areas of the vasculature. When these clots are located in the neurovascular system, these clots can lead to stroke. Recent technologies to deal with clot removal utilize devices designed to hold and capture the clot, followed by withdrawal of the device to physically remove these clots from the body. Several of these devices may fail to capture the clot in its entirety, or may promote clot fragmentation which may allow thrombus to dislodge and accumulate at another site, thus continuing the risk of stroke. In addition, several of these devices may promote endothelial denudation due to high friction between the device and the vessel wall. There is need for an obstruction removal device which reduces the likelihood of fragmented thrombus staying in the vasculature while maximizing the chance of mechanically capturing the clot, and limiting the risk of endothelial denudation.

SUMMARY OF THE INVENTION

In one embodiment according to the present invention, an obstruction removal device is described having a retriever and a sheath where said retriever and sheath are delivered through a delivery device.

In another embodiment according to the present invention, an obstruction removal device is described having a retriever and a sheath where said sheath is mounted external to a delivery device.

In another embodiment according to the present invention, an obstruction removal device is described having a retriever utilizing bipolar electrodes.

In another embodiment according to the present invention, an obstruction removal device is described having a charged retriever and an electrode with an opposing charge.

In another embodiment according to the present invention, an obstruction removal device is described having a charged retriever and a charged guidewire.

One aspect of the invention provides an obstruction removal device that includes a delivery device; a retriever slidably disposed within the delivery device and extendable out of a distal end thereof; and, a sheath positioned such that, after the retriever has captured an obstruction, the sheath is invertible over the retriever and the obstruction. The obstruction removal device may include a pusher connected to the retriever and usable to slide the retriever through the delivery device. The sheath may have a distal end connected to the pusher proximal of a proximal end of the retriever.

Another aspect of the invention provides a sheath that is disposed on an outer surface of the delivery device and has a distal end connected near a distal end of the delivery device. A restraining element may be associated with a proximal end of the sheath, releasably holding the proximal end of the sheath against the outer surface of the delivery device to prevent inversion until the inversion is desired.

Another aspect of the invention provides a method of removing an obstruction from a body lumen that includes navigating an obstruction retriever to an obstruction; capturing the obstruction with the retriever; inverting a sheath over the obstruction and the retriever; and, removing the obstruction from the body lumen.

The step of navigating an obstruction retriever to an obstruction may include navigating a delivery device containing the obstruction retriever in a collapsed configuration to the obstruction.

Capturing the obstruction with the retriever may involve retracting the delivery device relative to the retriever thereby allowing the retriever to expand.

Allowing the retriever to expand may be accomplished by allowing the retriever to expand within the obstruction.

Capturing the obstruction with the retriever may involve retracting the delivery device relative to the retriever thereby allowing the retriever to expand distal of the obstruction and pulling the retriever through the obstruction.

Inverting a sheath over the obstruction and the retriever may be caused by preventing distal movement of a distal end of the sheath while allowing distal movement of a proximal end of the sheath, for example by connecting a distal end of the sheath to a distal end of a delivery device. Alternatively, preventing distal movement of a distal end of the sheath may be effected by connecting a distal end of the sheath to a proximal end of the obstruction retriever.

Another aspect of the invention provides an obstruction removal device that includes a first component having at least one expandable engaging member and a flexible second component. The second component is associated with the first component such that the second component can be distally inverted over the first component. A delivery device may be included that slidably contains at least the first component.

The obstruction removal device may include a connector connecting a distal end of the second component to a proximal end of the first component.

The second component may be constructed using a mesh. Additionally, the second component may have a delivery configuration and an inverted configuration wherein in the delivery configuration, the second component is disposed on an outer surface of the delivery device. The second component may have a distal end that is fixed relative to a distal end of the delivery device.

In one aspect of the invention, the obstruction removal further includes a power source connected to at least the first component such that electricity may be delivered to an obstruction.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
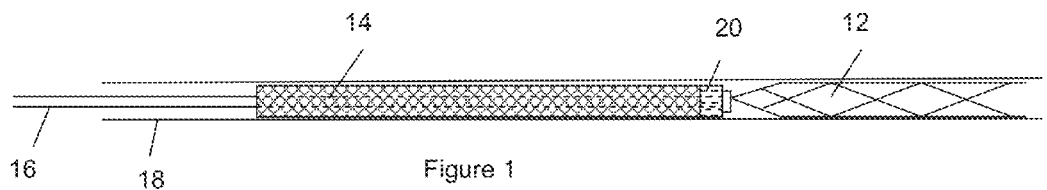
FIG. 1 is a plan view of an embodiment of an obstruction removal device of the invention in a collapsed or compressed configuration.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

For the purposes of the terminology described below, the terms clot, thrombus, embolus, and obstruction can be used synonymously. Though an obstruction removal device is described, the device can be used to capture clot, thrombus, embolus, foreign bodies, or other matter. Engaging members on the device can engage clot, thrombus, embolus, foreign bodies, obstructions, or other matter.

Figure 2:
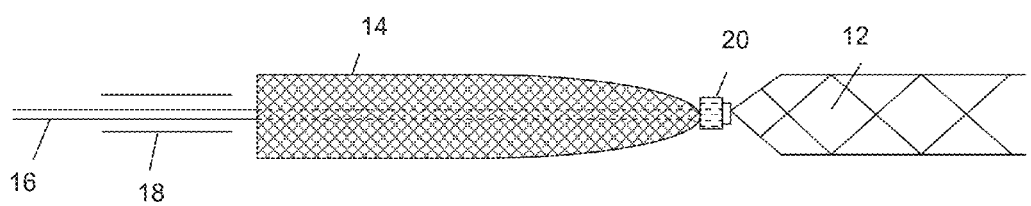
FIG. 2 is a plan view of the embodiment of FIG. 1 in an expanded, unrestrained configuration.

FIGS. 1-4 show one embodiment of an obstruction removal device comprising a retriever 12 and a sheath 14 both connected to junction 20. The delivery system used to deliver the obstruction removal device includes a catheter 18 through which the obstruction removal device is delivered to the target area within the vasculature. Pusher 16 is used to push the device through the catheter. Pusher 16 is connected to junction 20. Sheath 14 and retriever 12 thus move together in response to the movement of pusher 16 due to the shared connection to junction 20. In these figures retriever 12 is shown as a generally tubular body within an open distal end used to engage the clot, thrombus, embolus, or foreign body material. Retrieval component 12 can have a closed distal end, and can any number of different shapes. FIG. 1 shows the obstruction removal device in a compressed configuration as it would sit within a catheter, where sheath 14 and retriever 12 are compressed. FIG. 2 shows retriever 12 and sheath 14 in an expanded configuration when the catheter 18 is retracted. In the absence of any restraining force, such as that provided by a smaller catheter during delivery, retriever 12 and sheath 14 will adopt its natural expanded shape.

The materials comprising retriever 12 and sheath 14 are such that they allow these components to compress from their natural, expanded shape, and then adopt said natural, expanded shape when free of any constraining force. By way of nonlimiting example, retriever 12 may be made of a material such as nitinol, stainless steel, cobalt chromium, or combinations therein. Retriever 12 may also include a radiopaque material such as tantalum or platinum to aid in imaging.

Figure 3:
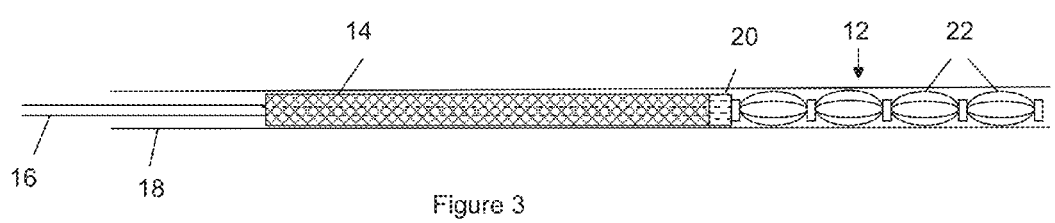
FIG. 3 is a plan view of an embodiment of an obstruction removal device of the invention in a collapsed or compressed configuration.
Figure 4:
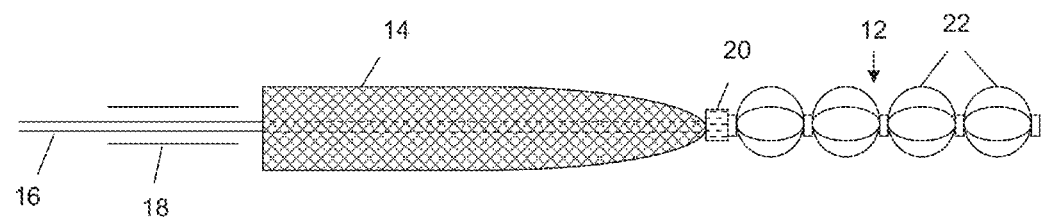
FIG. 4 is a plan view of the embodiment of FIG. 3 in an expanded, unrestrained configuration.

FIGS. 1-2 show the obstruction removal device having a retriever 12 wherein said retriever 12 is a generally tubular body. FIG. 1 shows the retriever 12 and sheath 14 in a collapsed, delivery configuration while FIG. 2 shows the retriever 12 and sheath 14 in an expanded, delivered configuration. FIGS. 3-4 show the obstruction removal device having a retriever 12 wherein said retriever has one or more engaging members 22 used to engage matter within the vasculature. FIG. 3 shows the retriever 12 and sheath 14 in a collapsed, delivery configuration while FIG. 4 shows the retriever 12 and sheath 14 in an expanded, delivered configuration. Though FIGS. 3-4 show four engaging members used on the retriever, fewer or more engaging members can be used. The engaging members of this embodiment will be described in more detail later.

FIGS. 1-4 show two possible retriever configurations, one involving a generally tubular body (FIGS. 1-2) and one involving one or more engaging members 22 (FIGS. 3-4). These two configurations are offered as way of example, though other retriever shapes and/or configurations are within the scope of the obstruction removal device of the present invention.

The sheath 14 may be made of any of a variety of materials. For example, the sheath 14 may be a mesh or a braid. Sheath 14 may be made of nitinol, stainless steel, or cobalt chromium wires, or combinations thereof. Other metals could also be used. Sheath 14 may include a radiopaque material such as tantalum or platinum to aid in imaging. The wires or fibers comprising sheath 14 may have a cross section selected from the group including, but not limited to, circular, elliptical, semi-circular, rectangular, square, polygonal, etc. The sheath 14 itself may be straight tubular or have a tapered shape and may have a consistent or variable pitch in its profile. In another example the mesh pattern could be cut from a solid metallic tube. The sheath could also be comprised of a polymer material. In one example it could be comprised of one or more polymer filaments would into a mesh pattern. In another example the sheath could be made of a solid polymer tube wherein regions are cut out to create a mesh or braid type pattern. The cutting operation could be performed via laser cutting or other known methods.

Figure 9:
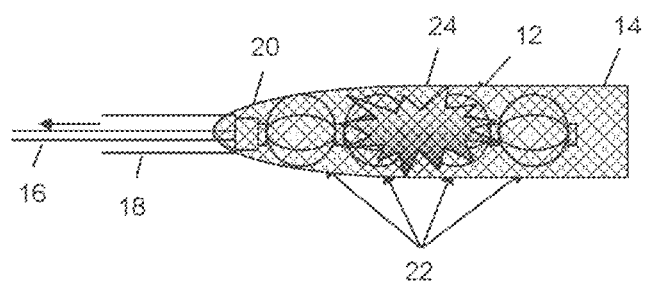
Figure 10:
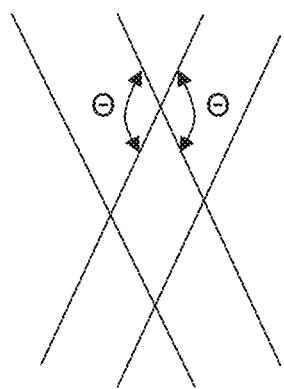
FIGS. 10-11 define braid angle convention used in the description herein of the configurations of the braid components of the sheath of the obstruction removal device.
Figure 11:
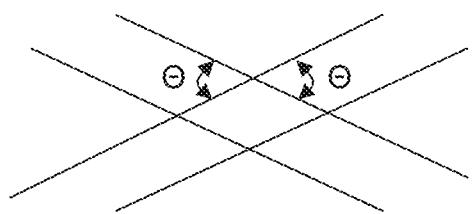

In one example the sheath 14 is made entirely from nitinol wires. In another example the sheath 14 is a combination of nitinol and platinum wires. In another example the sheath 14 is a combination of nitinol and tantalum wires. In another example the sheath 14 is made of cobalt chromium wires. In another example, various combinations therein of nitinol, tantalum, platinum, and cobalt chromium wires are used in the sheath 14. The sheath 14 can be braided from the wire material combinations listed above where the diameter range of the wires is between 0.0005"-0.003". The number of wires used in the sheath can range from 30-500. In one example, 96-192 wires are used in the sheath. The braid angle can be between 30-150 degrees. In one example a braid angle between 68-143 degrees may be used. In one example, the braid comprising sheath 14 is made of 50% nitinol wire with a diameter range of 0.001"-0.003", 30% tantalum wire with diameter range 0.002"-0.003" or 30% tantalum ribbon 0.002"×0.007", and 20% barbed or standard micro surgical suture with a diameter of 0.002"-0.005". The inclusion of suture material may support more effective attachment between the clot and the sheath 14. In another example the braid may be composed of nitinol with a diameter range of 0.0005"-0.001", tantalum wire with a diameter range 0.001"-0.0015" or tantalum ribbon 001"×0.003". Polymer microfibers may be included as well, or polymer microfibers may be used alone to make sheath 14. FIG. 10 shows an obtuse braid angle configuration while FIG. 11 shows an acute braid angle configuration. These configurations would be how the braid sits when proceeding longitudinally along the length of the sheath (i.e. left-to-right or right-to-left on the sheath of FIGS. 1-9). sheath 14 is preferably soft and highly foldable and adaptable. This allows the sheath 14 to easily invert or fold over itself.

Figure 5:
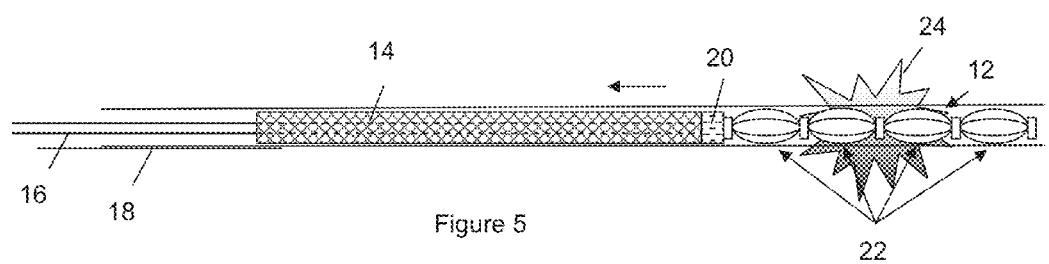
FIGS. 5-9 illustrate the obstruction removal device of FIGS. 3-4 during deployment, retrieval, and withdrawal operations in the vasculature system.
Figure 6:
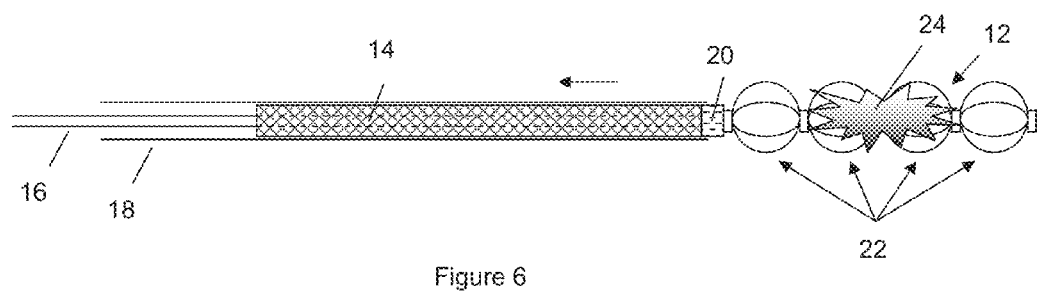
Figure 7:
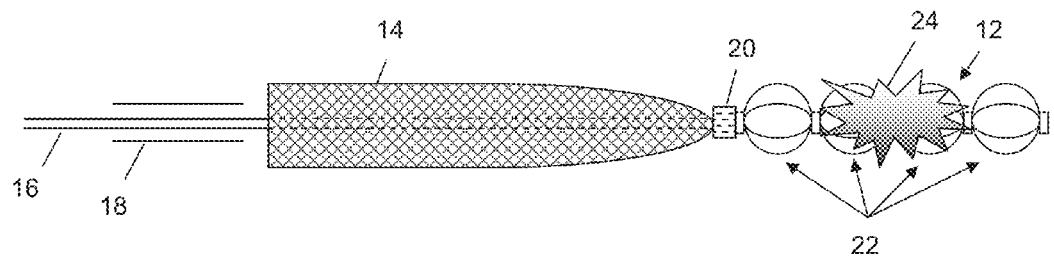
Figure 8:
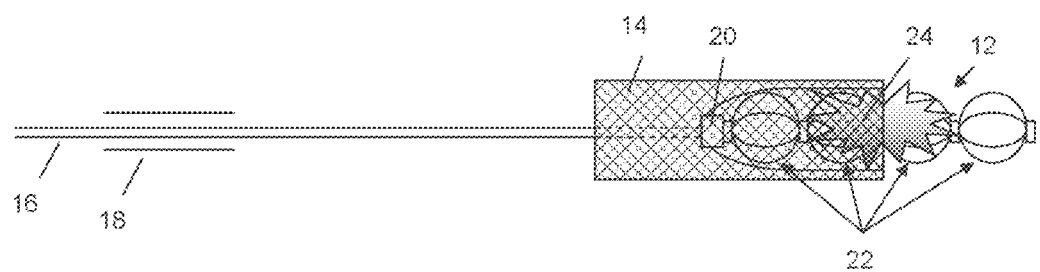

The sheath supplements the thrombus-capturing ability of the retriever by inverting itself over the retriever and the thrombus after the retriever has dislodged the thrombus from the blood vessel. This ensures that the entire thrombus is captured, even in the event that the thrombus breaks into smaller pieces. The sequence of events is shown in FIGS. 5-9 and described below. Generally, FIG. 5 shows the catheter 18 containing the retriever 12 and the sheath 14 contained therein placed such that the distal end of the catheter is past the targeted thrombus 24. In FIG. 6 the catheter 18 is retracted to allow the retriever to expand in and/or past the thrombus 24. The catheter 18, in FIG. 7, is retracted further so the sheath 14 is expanded. In FIGS. 8-9 the sheath inverts over itself to cover the thrombus 24 and the retriever 14.

As stated above, the sheath 14 is soft and pliable in order to adopt the configuration shown in FIGS. 8-9, where the sheath folds over the retriever 14. In these Figures delivery catheter 18 is retracted, exposing sheath 14. The natural flow of the blood will push sheath 14 outward (i.e. from a proximal to a distal direction, or left to right as shown in FIGS. 7-8), causing said sheath to envelope retriever 14. Since sheath 14 is connected to junction 20, the remaining unconstrained end is free to fold to the other side and overlap retriever 14. This adaptability is due to a combination of factors including the softness of the wires used to create the braid, the ratio of wire diameter to overall braid diameter, the braid angle used, and the shape of the sheath. The softness of the wires comprising sheath 14 also helps minimize friction between the retriever and the blood vessel wall when the sheath folds over retriever 12. As will be explained later, the engaging members 22 of the retriever 14 of the obstruction removal device shown in FIGS. 3-4 have particular properties to mitigate blood vessel damage during tracking of the device. The softness of sheath 14 helps to further mitigate any potential blood vessel damage during operation of the device.

One example of the method of operation of the obstruction removal device is as follows. A guide catheter is inserted into the vasculature and a guidewire is advanced through the guide catheter to the treatment site. A microcatheter is advanced over the guidewire to the treatment site. In one example the obstruction removal device is used to retrieve thrombus and the microcatheter in advanced through the clot to a point distal of the clot. The guidewire is removed, and the obstruction removal device is advanced through the microcatheter via pusher 16. Imaging techniques such as fluoroscopy can be used to aid placement of the device. The microcatheter is retracted, causing sheath 14 and retriever 12 to expand. The force applied to the sheath due to blood flow and the adaptable nature of sheath 14 will cause the sheath to envelope retriever 12, as shown in FIGS. 7-9. Retriever 12 captures the thrombus, and sheath 14 helps ensure the thrombus is held within the retriever and limits possible maceration of the thrombus. In one example, the device is positioned at a point just past the distal end of microcatheter 18 via pusher 16 and the device and microcatheter are withdrawn through the guide catheter. In one example the delivery means 18 is a hypotube instead of a microcatheter. Aspiration can also be used to aid in the clot retrieval procedure. This general procedure is shown in FIGS. 5-9 where the obstruction removal device is used to capture clot 24.

FIGS. 5-9 illustrate an example of a method of deploying the obstruction removal device. In this example, catheter 18 is delivered through the vasculature to the site of the clot 24. The obstruction removal device is pushed through the delivery device to the site of the clot. Although this particular example illustrates the obstruction removal device deployed in the middle of the clot, the device may be deployed in a location proximal of or distal of the clot location. In the device examples utilizing a retriever with engaging members, some engaging members 22 may sit distally past and/or proximally before the clot, depending on the size of the clot and the number of engaging members used on the obstruction removal device. Catheter 18 is then retracted, resulting in the engaging members of the retriever expanding and interacting with portions of the clot. The obstruction removal device can be manipulated by the operator via pusher 16. Once the clot is secured, the device can be withdrawn as described above. FIGS. 5-9 illustrate a particular example for illustrative purposes. Other delivery methods are contemplated within the scope of the invention, such as pushing the obstruction removal device from the delivery device. For the purposes of the figures, the device of FIGS. 3-4 is shown. However, the same general principle applies to the device of FIGS. 1-2 as well as to a device utilizing other potential retriever shapes/configurations.

Figure 12:
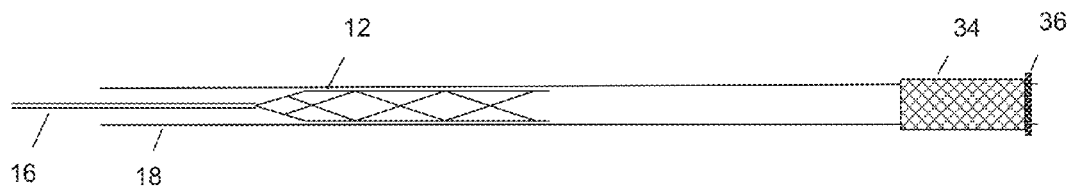
FIG. 12 is a plan view of an embodiment of an obstruction removal device of the invention in a collapsed or compressed configuration.
Figure 13:
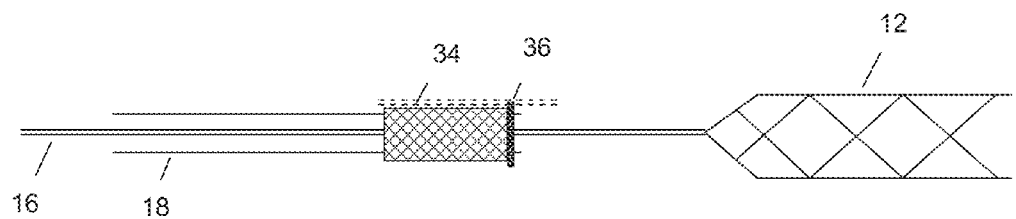
FIG. 13 is a plan view of the embodiment of FIG. 12 in an expanded, unrestrained configuration.
Figure 14:
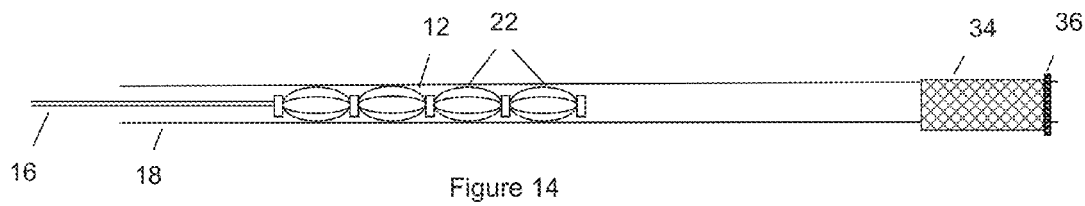
FIG. 14 is a plan view of an embodiment of an obstruction removal device of the invention in a collapsed or compressed configuration.
Figure 15:
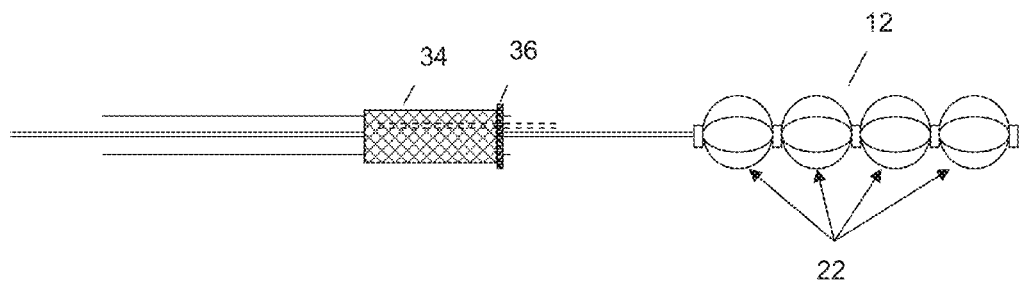
FIG. 15 is a plan view of the embodiment of FIG. 14 in an expanded, unrestrained configuration.
Figure 16:
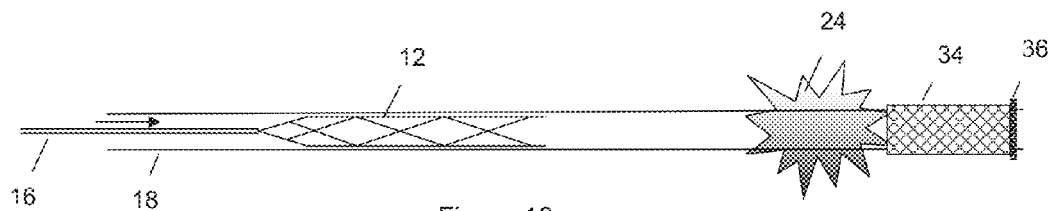
FIGS. 16-19 illustrate the obstruction removal device of FIGS. 12-13 during deployment, retrieval, and withdrawal operations in the vasculature system.
Figure 17:
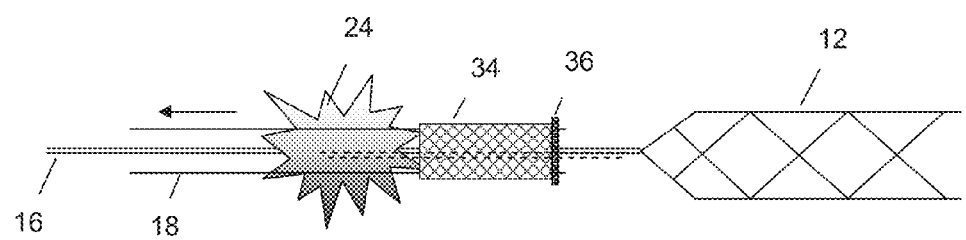

FIGS. 12-15 show another embodiment of an obstruction removal device comprising a retriever 12 and a sheath 34. Sheath 34 sits over the periphery of the distal portion of catheter 18. Retriever 12 is connected to pusher 16 and is delivered through catheter 18. The retriever assumes a collapsed configuration during delivery (FIGS. 12, 14) and an expanded configuration when unsheathed (FIGS. 13, 15). FIGS. 12-13 show a retriever formed of a generally tubular and open-ended body and FIGS. 14-15 show a retriever with one or more engaging members 22. Both retrievers shown are similar to the retrievers shown and described above in previous embodiments of the obstruction removal device. More detailed descriptions of the components of the retrievers are provided below.

Retriever 12 can adopt a number of shapes and/or configurations. A fixed end 36 is located at the distal portion of catheter 18, on the external surface of said catheter. Fixed end 36 sits at the distal end of sheath 34. The fixed end can be a separate circumferential piece of material, which is bonded to the external surface of catheter 18. The primary purpose of fixed end 36 is to provide a surface to contact the distal end of sheath 34 and prevent sheath 34 from flipping outward too quickly.

In the absence of any restraining force, sheath 34 may flip outward (similar to FIGS. 8 and 9) due to natural blood flow and the adaptable nature of the sheath. Fixed end 36 helps keep the sheath from flipping outward prior to contacting an obstruction, such as a clot. The distal portion of catheter 18 on which sheath 34 resides may also have a groove to accommodate sheath 34 and keep the sheath from flipping outward prematurely. Alternatively, the catheter may include another channel and a restraining element, such as a microsheath, may sit within the channel. On the distal end of the channel the restraining element can sit over the proximal end of sheath 34. The user may retract the restraining element by pulling on said element from the proximal end of catheter 18. Retracting the restraining element removes the restraining force from sheath 34. Alternatively, a combination of the restraining element and groove may be used.

Figure 18:
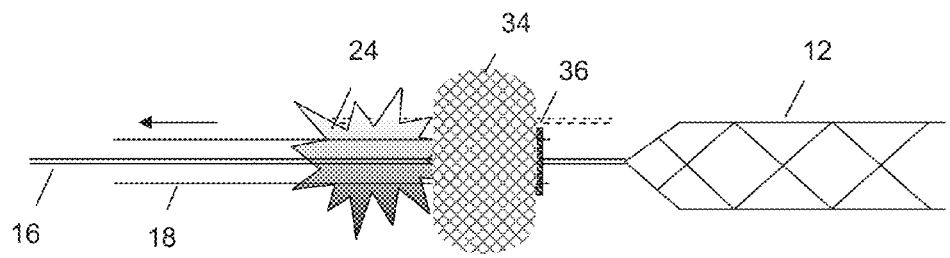
Figure 19:
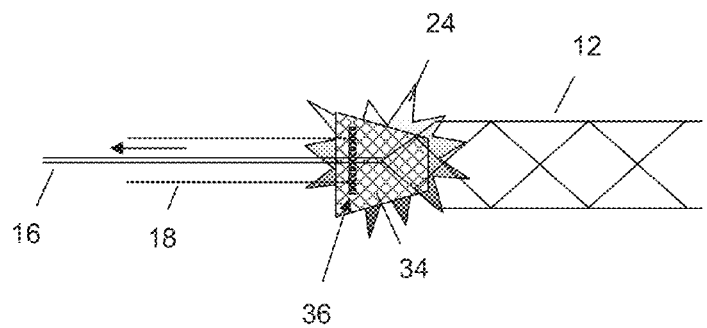

FIGS. 16-19 show the obstruction removal device utilized to capture a clot 24 within the vasculature. For the purposes of the figures, the device of FIGS. 12-13 is shown. However, the same general principle applies to the device of FIGS. 14-15 as well as to a device utilizing other potential retriever shapes/configurations. Delivery device 18 is delivered through the vasculature and the pusher 16 connected to the proximal end of retriever 12 is used to navigate the retriever. The delivery device, in this case catheter 18, is navigated to a position where sheath 34 sits just distal to the obstruction, in this case clot 24. Retriever 12 is then pushed out of catheter 18 to assume its expanded configuration. Catheter 18 is subsequently retracted, and any restraining force on the sheath (such as the restraining element described above) is removed. The retraction of catheter 18 will cause the sheath to flare outwards as it is compressed between fixed end 36 and the distal portion of clot 24, as shown in FIG. 18. Once enough compressive force is applied on the sheath it folds over fixed end 36 and folds backwards due to the compliant nature of the sheath. Catheter 18 is simultaneously retracted so the distal end of catheter 18 sits within the clot (FIG. 19). Clot 24 is caught between sheath 34, which is attached to catheter 18, and the proximal portion of retriever 12. Catheter 18 can now be withdrawn, with the clot secured between sheath 34 and retriever 12.

One example of the method of operation of the obstruction removal device is as follows. A guide catheter is inserted into the vasculature and a guidewire is advanced through the guide catheter to the treatment site. A microcatheter is advanced over the guidewire to the treatment site. In one example the obstruction removal device is used to retrieve thrombus and the microcatheter is advanced through the clot to a point just distal of the clot. The guidewire is removed and the retriever is advanced through the microcatheter. Imaging techniques such as fluoroscopy can be used to aid placement of the device. In one example the microcatheter is pushed through the clot and positioned at a point just distal of the clot. The retriever is pushed through the distal end of the microcatheter and positioned via the pusher. The microcatheter is retracted, causing the sheath to flare out and eventually fold over the fixed end. The microcatheter is retracted and the retriever is manipulated via the pusher to position the clot between the sheath and retriever. The microcatheter and obstruction removal device are then withdrawn through the guide catheter. In one example the delivery means 18 is a hypotube instead of a microcatheter. Aspiration can also be used to aid in the clot retrieval procedure. This general procedure is shown in FIGS. 16-19 where the obstruction removal device is used to capture clot 24.

Figure 20:
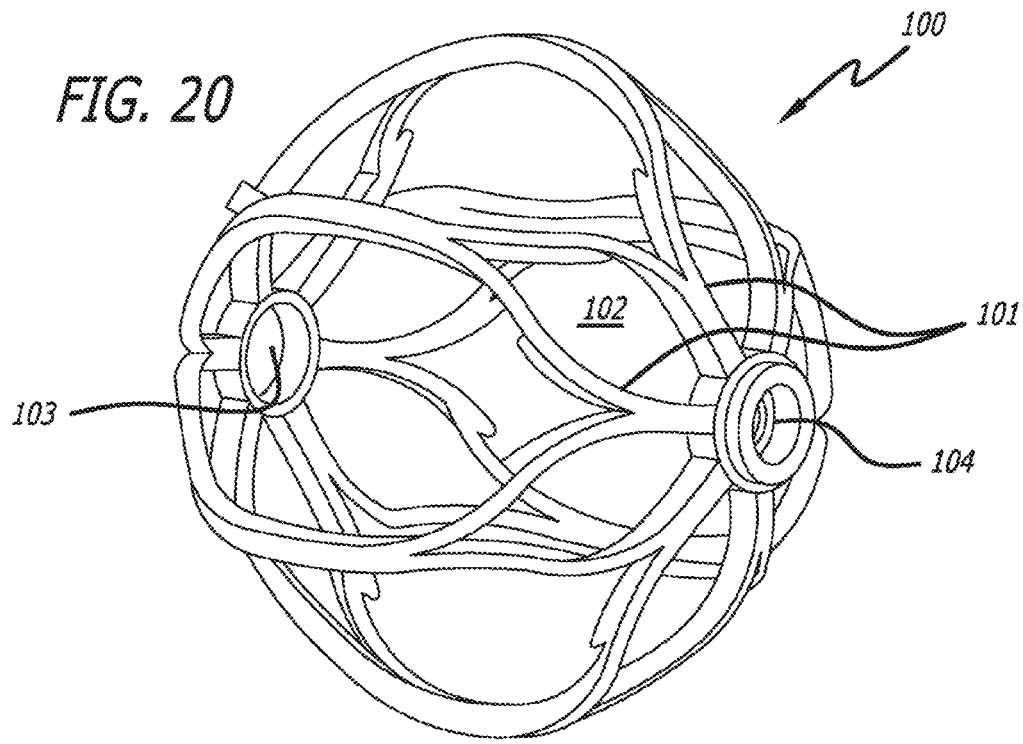
FIG. 20 is an engaging member used in an obstruction removal device.
Figure 21:
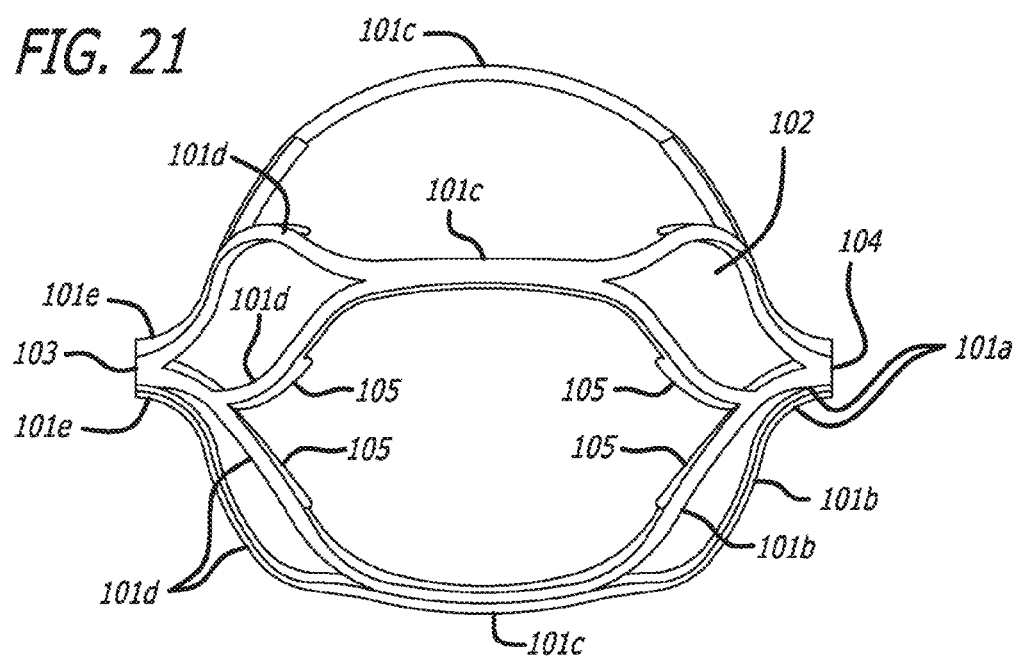
FIG. 21 is another view of the engaging member used in an obstruction removal device.

FIGS. 20 and 21 show an engaging member 100 used with the obstruction removal device of the present invention. One or more engaging members are used as part of an obstruction removal device in order to engage thrombus which can accumulate within a vascular system. General engaging member shapes can include, but are not limited to, round, oval, elliptical, hourglass, spherical, basket, stent, countered, rectangular, prismatic, cage. Each engaging member 100 has a number of struts 101 which define a number of cells, or openings 102, and a pair of opposing holes 103 and 104. For the sake of convention, hole 103 is a distal hole and hole 104 is a proximal hole.

Each engaging member may be uniquely configured with different struts, cells, cell sizes, materials, and/or shapes. The strut design can have a linear, wave, sinusoidal, or zig-zag pattern, or can have a non-symmetrical design (i.e. where struts on one side of the engaging member are not mirrored on the other side of said engaging member). The non-symmetrical strut design may help facilitate a rotational component on the member as it travels through a vessel, by shifting the center of gravity from the geometric center of the engaging member. This ease of rotation makes it easier for the engaging members, and therefore the obstruction removal device, to move more easily through the anatomy, especially after the clot has been engaged and the device is being pulled back through the vasculature. This ease of rotation can also limit the amount of damage to the vessel wall due to excessive contact friction by limiting the damage to a particular section of the wall. The engaging members may have either identical or unique designs on each end of the engaging member. This may be done by varying shape of the struts and/or cells, and/or varying the cell density of each end, thus—for example—allowing for large cell sizes on one end and smaller cell sizes on the opposing end. This variability may allow for different properties to allow for enhanced ability to engage the clot, or enhanced ability to track the obstruction removal device and deployed engaging members through the vessel.

FIG. 21 shows an engaging member 100 having a plurality of struts 101 having different thicknesses. More specifically, a plurality of end struts 101a branch out from the material defining proximal hole 104, and one or more of these struts 101a split to form struts 101b. Struts 101b are shown with features 105 protruding therefrom. Features 105 may be any interruption in the otherwise continuous surface of the strut 101. Non-limiting examples include barbs, bumps, protrusions, spikes, branches, nubs, and the like. The struts 101b are then shown as joining an adjacent struts 101b to form thicker struts 101c, which then split again to form additional struts 101d, also shown as having features 105. These struts 101d then join together again to form thicker struts 101e, which are connected to define distal hole 103. As such, it is seen that, in this particular embodiment, the struts interconnect to form a web of struts that span from the proximal hole 104 to the distal hole 103.

Another strut configuration could utilize a single strut pattern. An example includes a contiguous, helical strut configuration running between the proximal and distal ends of the engaging member, or running between a portion of the length spanning the proximal and distal ends of the engaging member.

Each engaging member has a collapsed configuration when sheathed within a delivery device, and takes on an expanded configuration as shown in FIGS. 20 and 21 when unsheathed. Each engaging member can be self-collapsible and self-expandable based on whether an external force is applied to constrain it (as would be the case when sheathed in a delivery device), or no constraining force is present (as would be the case when unsheathed).

The engaging member may be formed from nitinol, or a similar material, and may be laser cut to achieve the profile shape. Other materials and other cutting and/or machining processes would fit within the scope of the invention.

The distal and proximal holes, 103 and 104, on respective distal and proximal end of the engaging member, may facilitate placement of a common rod on which each engaging member sits, or they may fit separate connection pieces to connect multiple components of the obstruction removal device with the respective engaging members.

Figure 22:
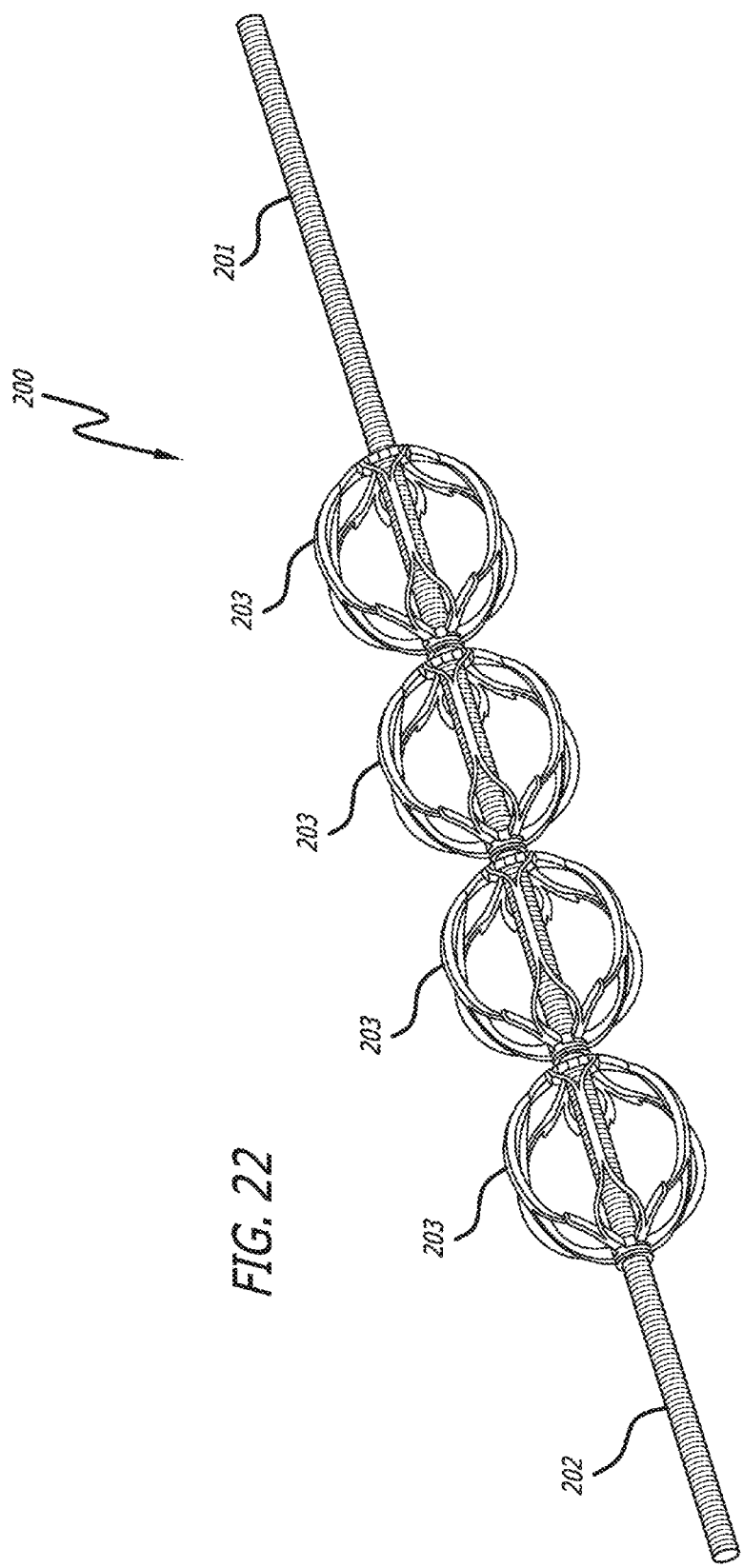
FIG. 22 is an obstruction removal device according to one embodiment of the present invention.

FIG. 22 illustrates an obstruction removal device 200 according to one embodiment of the present invention. The obstruction removal device comprises a proximal core structure 201 at one end of the device, a distal bumper structure 202 connected to the proximal core structure 201, and one or more engaging members 203 mounted to the distal bumper structure 202. In one example, the device is pushed and/or pulled from the core structure 201 end. A pusher may sit under the core structure, or the core structure itself may act as a pusher.

Core structure 201 may be made of a variety of materials, including, but not limited to, nitinol, stainless steel, cobalt chromium, or a polymeric material such as PTFE, Pebax, TPE, Engage, polyethylene, or other similar materials. Core structure configurations can include, but are not limited to, a coil, a braid, or a coil/braid combination.

The bumper structure 202 may be made of a radiopaque material, including, but not limited to, platinum, tantalum, palladium, or other similar material. A radiopaque material is preferred to make imaging of the device easier during the device insertion procedure, although non-radiopaque materials may also be used. The engaging members being mounted to the bumper structure, where the bumper structure is made of a radiopaque material, aids in imaging the device during the clot removal procedure. The engaging members may be mounted to the bumper structure in several ways. For example, the bumper structure may have a threaded outer profile, where the holes of the engaging members have a corresponding receiving structure to rotatably mate to the threaded bumper structure profile. Alternatively, the bumper structure may have a non-threaded outer configuration, and the engaging members may be affixed to the bumper structure by a heat treatment procedure, such as welding. Other mechanical means or other heat treatment procedures can also be used to affix the engaging members to bumper structure.

Figure 23:
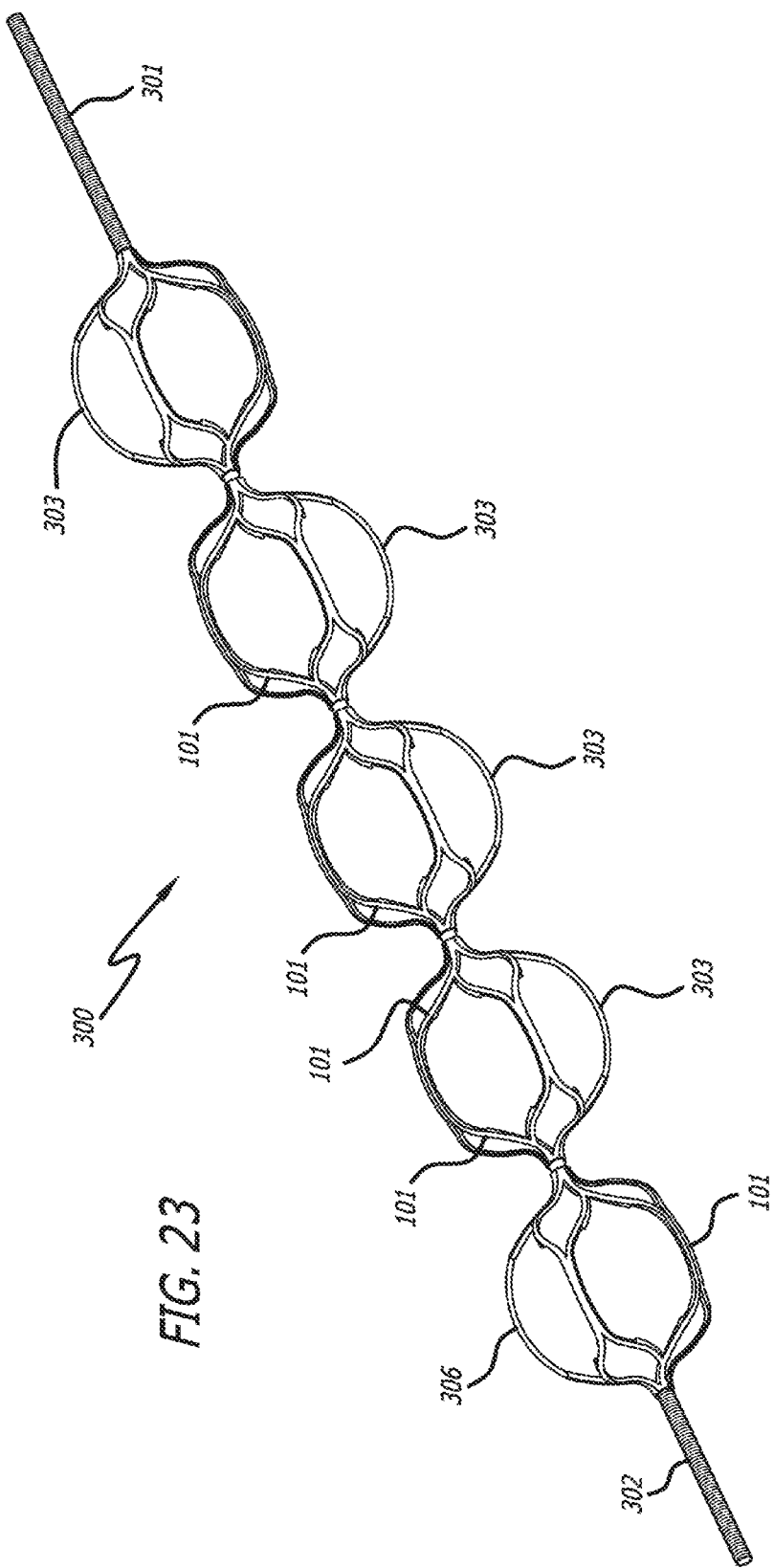
FIG. 23 is an obstruction removal device according to another embodiment of the present invention.

FIG. 23 illustrates an obstruction removal device 300 according to another embodiment of the present invention. The obstruction removal device 300 includes a proximal structure 301 connected to one or more engaging members 303. There may be a distal structure 302 attached to a distal-most engaging member (labeled as 306 for clarity, though it may be structurally the same or different as the other engaging members 303). The one or more engaging members 303 are connected to the proximal structure in such a way as to allow the one or more engaging members 303 to rotate independently of the proximal structure 301. The one or more engaging members 303 may be linked together to allow the engaging members 303 to rotate independently of each other as well, as discussed in more detail below. The obstruction removal device 300 is preferably pushed/pulled from one end of the proximal structure 301, thus the terms proximal portion structure and distal structure are used relative to the pushing/pulling end. Proximal structure 301 can act as the pusher 18 in FIGS. 1-9 which is connected to junction 20. Although five engaging members are illustrated in the figure, fewer or more engaging members can be used. Like all of the embodiments described herein, the engaging members 303 are constructed with one or more struts 101, as described above.

Figure 24:
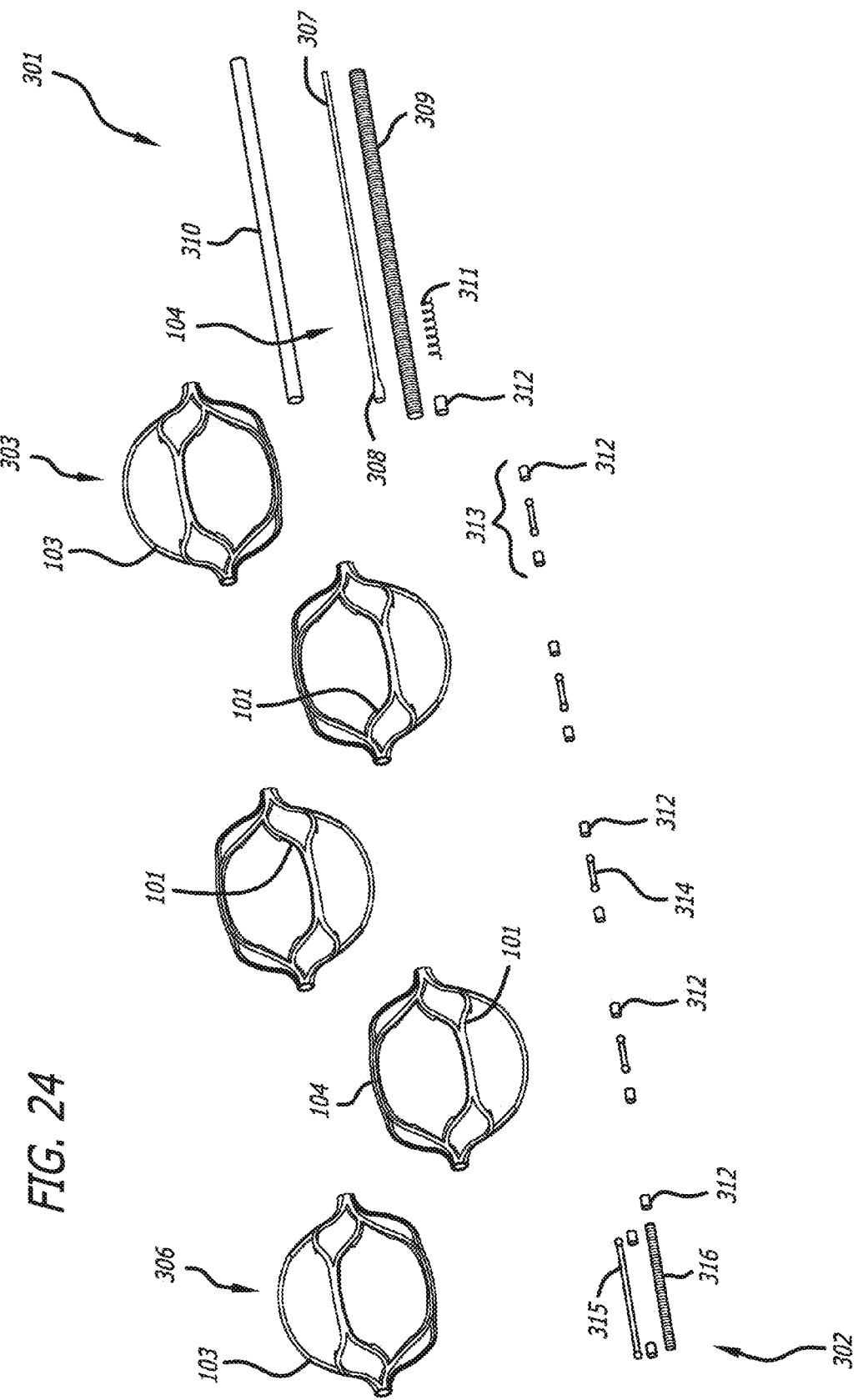
FIG. 24 is an exploded view of the obstruction removal device shown in FIG. 4.

FIG. 24 illustrates an exploded view of an embodiment of the obstruction removal device 300 of FIG. 23. The proximal structure 301 may include a core wire 307 which sits under a coil 309, which may sit under a tube 310. The core wire 307 includes a flared end 308. The core wire 307 may be made of nitinol, or a similar material, although other materials are within the scope of the invention. The coil 309 may be made of tantalum, or other radiopaque materials, although non-radiopaque materials may also be used. The tube 310 may be made of PET, or other polymeric material, although non-polymeric materials may be used as well. The proximal structure also includes another coil 311 which is preferably more gapped than coil 309, and can be made of a similar material. Coil 311 sits between core wire 307 and the over-coil 309, and helps center core wire 307 within coil 309. Proximal structure 301 is connected to a proximal engaging member 302, which can in turn be connected to another engaging member if more than one engaging member is used in the obstruction removal device.

The distal structure 302 includes a monofilament 315, which sits under a coil 316. Alternatively, multiple monofilaments can be bonded together to produce a monofilament structure 315. The monofilament 315 can be made of a stretch-resistant polymer such as Engage, although other materials may be used. The coil 316 may be made of tantalum, or other radiopaque materials, although non-radiopaque materials may also be used. Adhesive, preferably UV curable adhesive, 317 is used at both ends of the coil structure 316 in order to keep the monofilament 315 integral within the coil 316. In one example, the distal structure can act as a guidewire.

A distal structure 302 may be connected to the distal-most engaging member 306. This distal structure may be radiopaque in order to aid in imaging of the device during deployment. In the embodiment of FIG. 24, the coil of the distal structure 302 fits within the hole 103 of the distal-most engaging member 306, and a retaining piece 312 fits on the other end to keep the distal portion 302 integral with engaging member 306. The retaining piece is welded within the interior of the structure of hole 103. The engaging member 306 can still rotate. The retaining piece may be of a tubular construction, and may be made from nitinol, although similar materials can also be used. In order to aid in imaging, the retaining piece may be made from nitinol filled with a radiopaque material. Alternatively, the retaining piece may be coated with a radiopaque material to aid in imaging of the device during the procedure. Alternatively, the retaining piece may be made of a radiopaque material.

Figure 25:
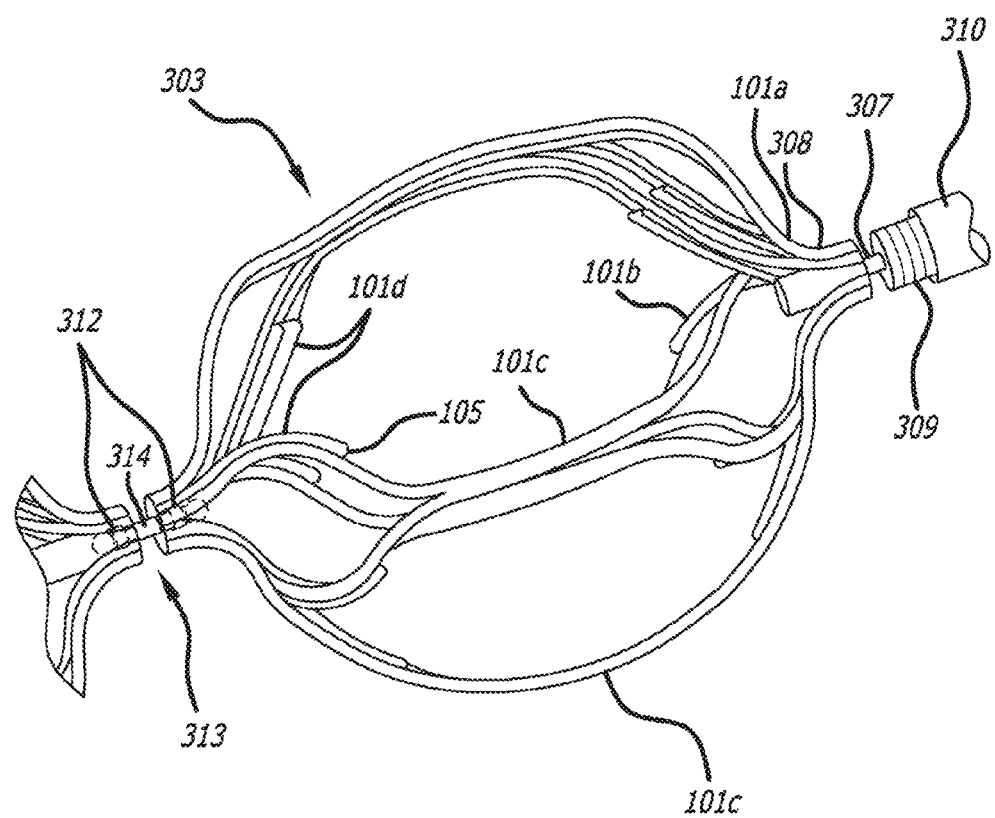
FIG. 25 is a magnified view of the proximal engaging member of the obstruction removal device of FIGS. 4 and 5.

The connection mechanism used to connect the engaging members together is shown in FIGS. 24 and 25. FIG. 25 illustrates the connection structure of engaging member 303, which is connected to the proximal structure 301 of the obstruction removal device.

The connection mechanism includes a link 313 with two flared ends 314, and retaining pieces 312. The link 313 may be made of stainless steel, although similar materials may be used. The flared ends extend within the opposing holes 103, 104 of the engaging members being connected, and the retaining piece 312 fits next to the flared end 314 to secure the link 313 within the hole of the engaging member. This connecting structure is used to connect the engaging members together, if more than one engaging member is used in the obstruction removal device. Retaining piece 312 is welded to the hole, and the link can rotate while secured within the hole of the engaging member. The engaging members may independently rotate.

Engaging member 303 is also connected to the proximal structure 301, as shown in FIGS. 24 and 25. The flared end 308 of the core wire sits past hole 104 of engaging member 303 and a retaining piece 312 sits over the core wire 307 to secure the proximal structure 301 to engaging member 303, where retaining piece 312 is welded within hole 104. A smaller, gapped coil 311 sits within the distal end of coil 309 and serves to help center the core wire 307 within the coil 309.

In one example, the connecting piece 313 is placed within the hole structure, and retaining piece 312 is welded into the hole over the connecting piece. The flared end 313 can subsequently be laser welded on the end of the connecting piece. In another example, the retaining piece 312 is welded into the hole and the connecting piece is placed within, and the flared end is laser welded. Although laser welding is specified, other similar heat treatment techniques can be utilized as well. This procedure can also be utilized at the end of core wire 307 to produce flared end 308, and to connect proximal-most engaging member 303 to the proximal portion 301 of the device. In one example, this procedure can be utilized at the end of the coil 316 when connecting the distal portion of the device to distal-most engaging member 306.

Each engaging member has a rotational component; this ability to rotate can aid in capturing the thrombus and navigating the vessel. This can also help limit the amount of endothelial denudation that may occur as the device is being pushed and/or pulled through the vessel, by helping to limit any excessive forces that build up due to excessive contact friction between the struts and the vessel wall. The engaging members may also be configured to have a more rounded, smoother profile (as illustrated in the figures) which would eliminate any sharp edges on the engaging members which may otherwise promote denudation due to high contact friction. Furthermore, due to the space between the engaging members, less material physically contacts the vessel than other designs which may utilize, for example, a longer one-piece clot engaging unit. Less material contacting the vessel will also serve to limit endothelial denudation during the clot removal procedure.

In one example, the proximal portion 301 of the obstruction removal device can include means to detach the engaging members from the obstruction removal device. The detachment means can be included on the portion of the proximal portion 301 contacting engaging member 303 (the proximal-most engaging member) and can include electrolytic, mechanical, thermal, or other means known in the art to induce severing and/or degradation of a linkage.

One or more of the engaging members may actively engage the clot, while other members can sit either distally beyond, or proximally before, the thrombus—depending on the size of the clot and the number of engaging members utilized on the device. Due to the potential variability in the individual shape and/or profile of each engaging member, as well as the number of engaging members used in the obstruction removal device compared to the size of the clot, one or more engaging members may sit distally past the clot and have a denser cell configuration to act as a filter for catching thrombus that may dislodge when capturing the clot utilizing the obstruction removal device. The engaging member(s) which act as a filter may have a mesh configuration; said mesh configuration can be throughout the whole engaging member or be located on one particular side of the engaging member, in order to maximize the chances of catching loose thrombus without the thrombus dislodging. In one example, the engaging member(s) which act as a filter has a denser cell configuration on the more-distal portion of said member in order to catch thrombus dislodged from interaction of the more proximal engaging members with the clot. This arrangement can be useful when the more proximal engaging members interact with the clot and portions of the clot macerate. The more distal engaging members with the filter configuration can catch macerated thrombus that otherwise might accumulate in the bloodstream. The engaging members which act as a filter may be formed from nitinol, stainless steel, or similar materials. Alternatively, they may be formed from laser cut polymers. Alternatively these engaging members acting as filters may have an inverted braid configuration, or other basket-type configurations, or other configurations known within the embolic protection device art. One or more of the engaging members may also be composed of a thrombogenic material, or may be coated with a thrombogenic material in order to aid in the clot retrieval procedure, by promoting adhesion between the engaging member and the thrombus. Alternatively, an anti-thrombogenic material can be used, or an anti-thrombogenic coasting can be used in order to help dissolve a portion of the clot that is in contact with the engaging members. This can be useful with, for instance, retrieval operations involving a large clot.

Figure 26:
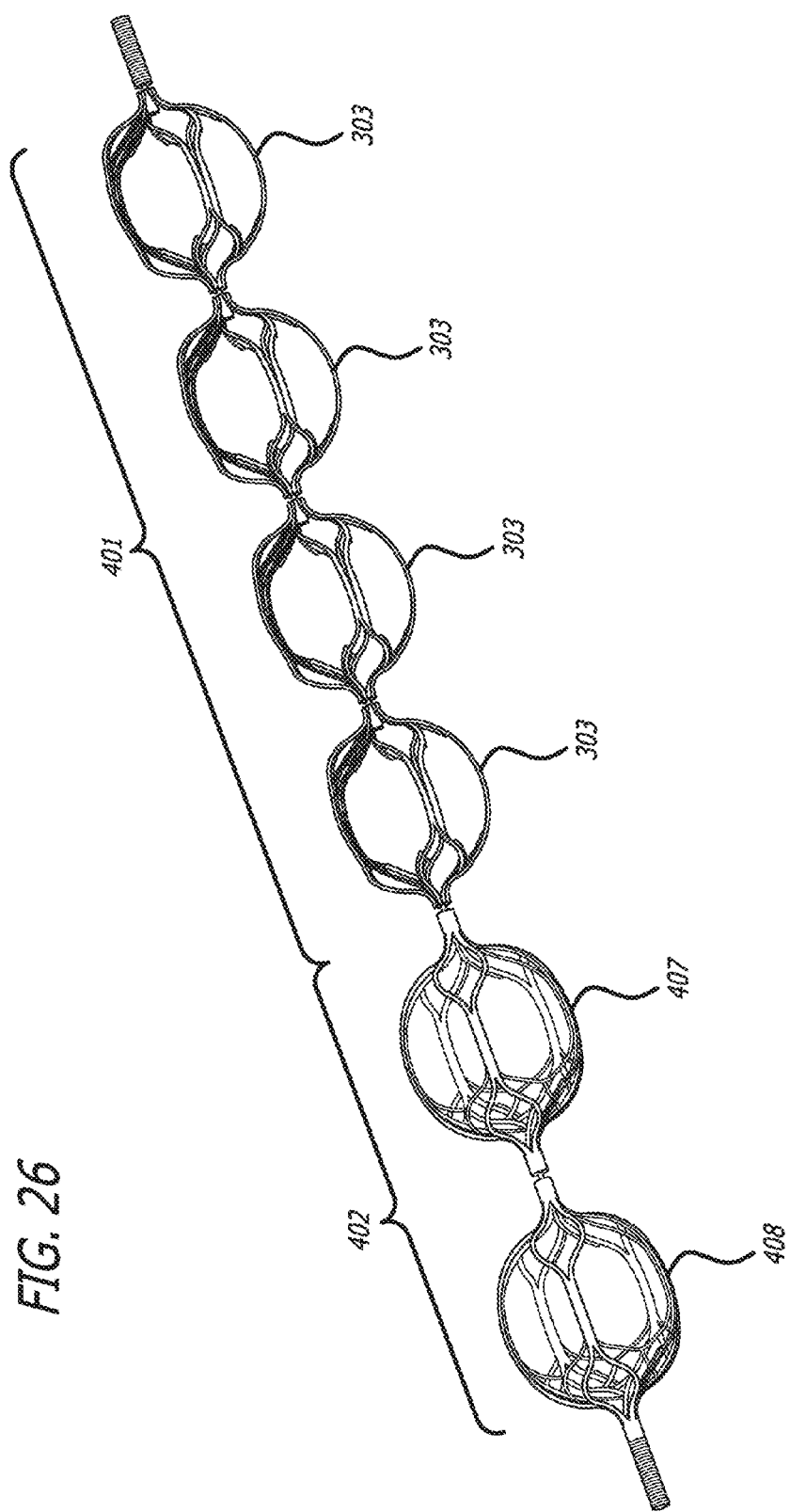
FIG. 26 is an obstruction removal device according to another embodiment of the present invention.
Figure 27:
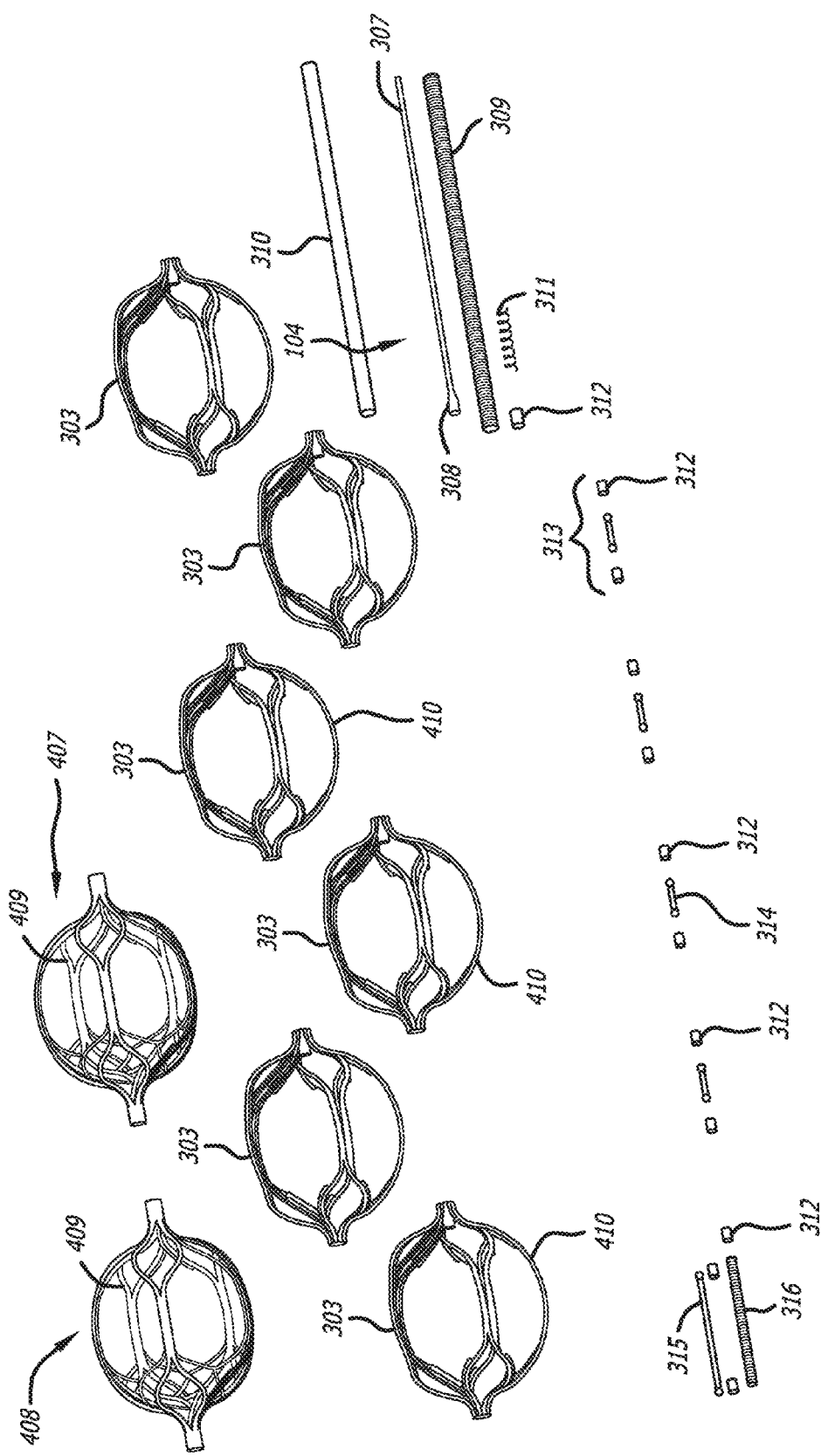
FIG. 27 is an exploded view of the obstruction removal device shown in FIG. 26.

FIGS. 26 and 27 illustrate another embodiment of the obstruction removal device utilizing one or more engaging members which act as a filter in order to catch thrombus that may become dislodged during the clot removal procedure. FIG. 26 illustrates the obstruction removal device, with a proximal portion 401 and distal portion 402. The proximal portion includes engaging members 303. The distal portion includes engaging members 407 and 408. The distal engaging members 407 and 408 have a denser cell configuration to act as a filter to trap dislodged thrombus which may shear off during the clot removal procedure, the clot removal procedure being generally described above. The denser cell configuration is due to an inner and outer structure used to form the engaging member, as illustrated in FIG. 27. As illustrated in FIG. 27, the two distal engaging members 407 and 408 are each composed of an inner structure 409 and outer structure 410, where the inner structure may nest within the outer structure. The inner structure 409 and outer structure 410 which comprise the distal engaging members 407 and 408 may be made from laser cut nitinol, or a similar material. The proximal portion 401 and distal portion 402 are configured the same as the embodiment presented in FIGS. 23-24, as are the linkages between each of the engaging members, although this filtering engaging member structure can be applied to any of the engaging members presented in any of the presented obstruction removal device embodiments.

Figure 28:
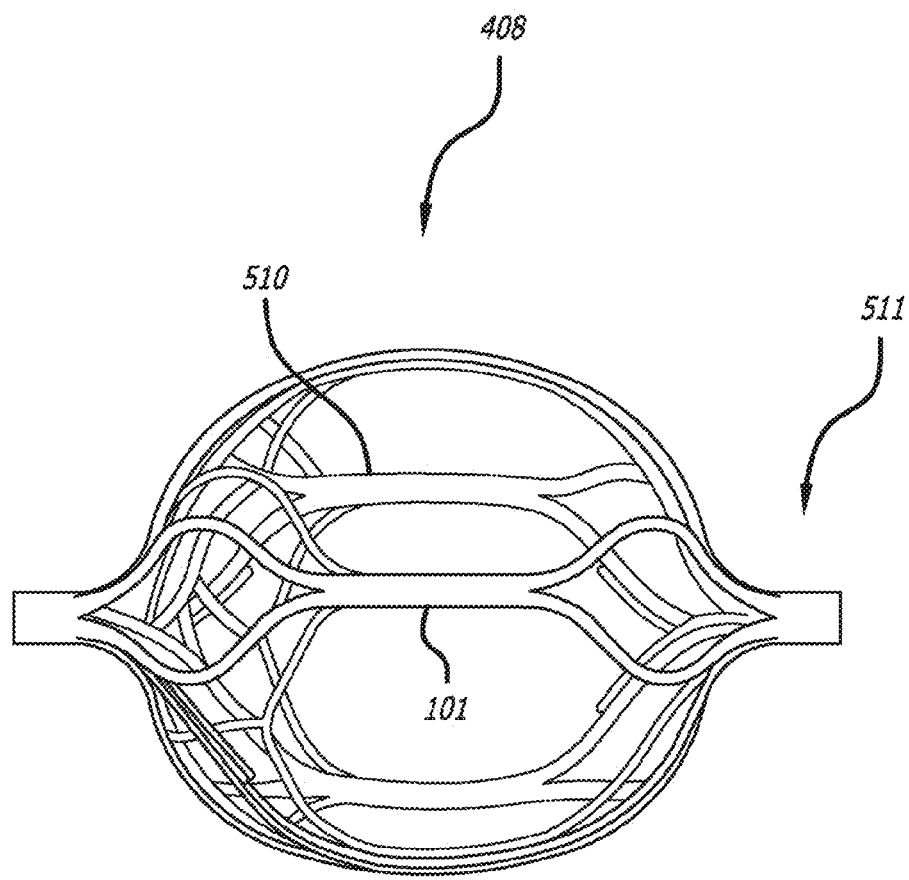
FIG. 28 is one of the distal engaging members used in the device shown in FIGS. 26 and 27.

The cell pattern may be slightly offset on the inner and outer structure in order to create a denser cell profile when the inner structure is nested within the outer structure. As shown in FIG. 28, the distal part 510 of the engaging member 408 has a denser cell profile than the proximal part 511 in order to catch dislocated thrombus which may escape during the clot removal procedure. This arrangement can be useful when the more proximal engaging members interact with the clot and portions of the clot macerate. The more distal engaging members with the filter configuration can catch macerated thrombus that otherwise might accumulate in the bloodstream. Although FIGS. 26 and 27 illustrate two engaging members having the inner and outer structure to act as a filter, more or fewer engaging members can have this filter structure.

Figure 29:
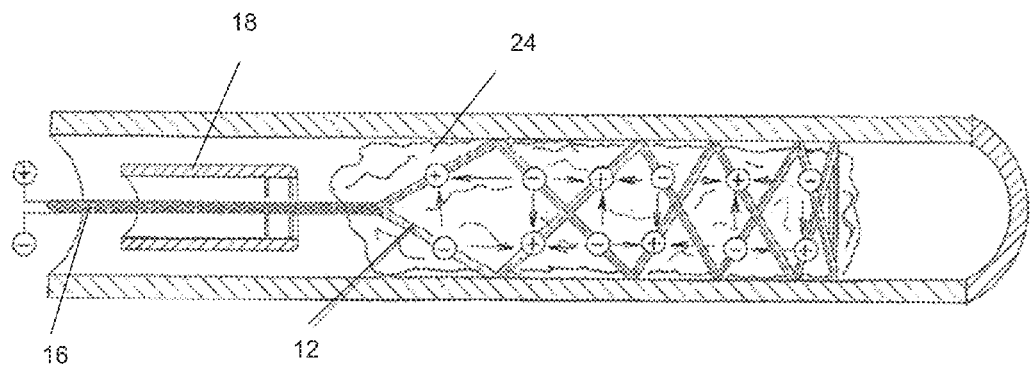
FIG. 29 illustrates an embodiment of an obstruction removal device of the invention.
Figure 30:
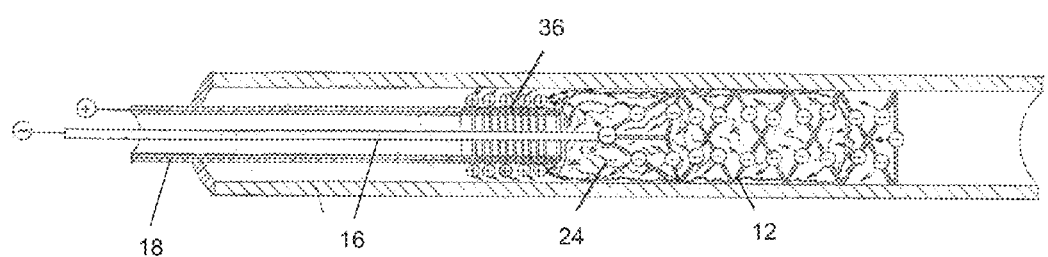
FIG. 30 illustrates an embodiment of an obstruction removal device of the invention.
Figure 31:
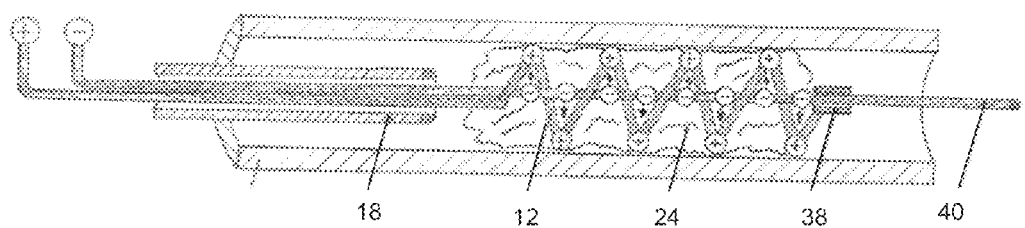
FIG. 31 illustrates an embodiment of an obstruction removal device of the invention.

FIGS. 29-31 show three additional embodiments of an obstruction removal device utilizing a retriever and electricity. The inclusion of electricity helps dissolve the clot while the retriever helps grasp and pull the clot, such a design would be useful for particularly large clots which are difficult to grasp completely with just a retriever. The inclusion of electricity would help dissolve portions of the clot making retention of the clot more practical. The retriever is self-collapsible and self-expandable, adopting a collapsed configuration when in the catheter and an expanded configuration when not compressed.

FIG. 29 shows another embodiment of the obstruction removal device comprising a retriever 12, which is connected to pusher 16. Each arm of retriever 16 comprises bipolar electrodes. The alternating positive/negative charge create electron flow between the various charged portions, the current generated due to this electron flow helps to dissolve portions of the clot.

FIG. 30 shows another embodiment of the obstruction removal device comprising a retriever 12 connected to a pusher 16. The retriever utilizes electrodes and the retriever as a whole has a particular polarity. In one example shown in the FIG. 30 the charge is negative. An electrode 36 is situated at the distal end of catheter 18. Electrode 36 has an opposing charge, which in the case of FIG. 30 is a positive charge. The opposing charge between retriever 12 and electrode 36 induces a current due to electron flow. The induced current will help lead to clot dissolution. In another example, the retriever has a positive polarity and the electrode has a negative polarity.

FIG. 31 shows another embodiment of the obstruction removal device utilizing an over-the-wire concept. The device comprises a retriever 12 and guidewire 40. The guidewire runs through the retriever and is polarized. By way of example, the guidewire is shown with a negative charge. The retriever 12 is polarized and has an opposite charge, in this example, a positive charge. The retriever 12 is connected to a marker 38. The marker 38 may be radiopaque to aid in visualization. The marker may slide over guidewire 40 in one example, in another example it is in a fixed position. The opposing charge between the guidewire portion 40 and retriever 12 induces a current due to electron flow. This induced current will help lead to clot dissolution. In another example, the guidewire has a positive charge and the retriever has a negative charge.

In one example the device mentioned in the all the previously described embodiments can be used to retrieve clots, thrombus, or embolus within the vascular system. In another example, the device mentioned in all the previously embodiments can be used to retrieve foreign objects. Circumstances may arise where foreign objects, such as embolic coils normally used to fill an aneurysm, may break off or otherwise become detached within the vasculature. The device can be used to retrieve the foreign body utilizing a procedure similar to the procedure used during obstruction removal.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An obstruction removal device comprising:
   a delivery device;
   a retriever slidably disposed within said delivery device and extendable out of a distal end thereof, said retriever including a plurality of engaging members arranged end-to-end and connected together such that said engaging members are able to rotate independently of each other;
   a pusher connected to said retriever and usable to slide said retriever through said delivery device;
   a self-expanding sheath positioned on an outside surface of said delivery device such that, after said retriever has captured an obstruction, said sheath is invertible over said retriever and said obstruction; and,
   wherein said delivery device includes a restraining element that sits over a proximal end of said sheath, preventing said sheath from inversion until said restraining element is retracted and said sheath is released.

2. The obstruction device of claim 1 wherein said sheath has a distal end connected to said delivery device.

3. A method of removing an obstruction from a body lumen comprising:
   navigating an obstruction retriever, and a sheath on an outside of a delivery device containing said obstruction retriever, through and distal of an obstruction, said sheath having a proximal end held to said delivery device with a restraining element, and said obstruction retriever including a plurality of engaging members arranged end-to-end and connected together such that said engaging members are able to rotate independently of each other;
   capturing said obstruction with said retriever by releasing said sheath from said restraining element and retracting said delivery device back through said obstruction, thereby causing said sheath to invert;

and,
removing said obstruction trapped between said sheath and said obstruction retriever from said body lumen.

4. The method of claim 3 wherein navigating the obstruction retriever comprises navigating the delivery device containing said obstruction retriever in a collapsed configuration to said obstruction.

5. The method of claim 4 wherein capturing said obstruction with said retriever comprises retracting said delivery device relative to said retriever thereby allowing said retriever to expand.

6. The method of claim 5 wherein allowing said retriever to expand comprises allowing said retriever to expand distal of said obstruction.

7. The method of claim 4 wherein capturing said obstruction with said retriever comprises retracting said delivery device relative to said retriever thereby allowing said retriever to expand distal of said obstruction and pulling said retriever through said obstruction.

8. The method of claim 3 wherein the distal end of the sheath is attached to the delivery device.

9. An obstruction removal device comprising:
a first component having a plurality of expandable engaging members arranged end-to-end and able to rotate independently of each other and advanceable through a catheter; and,
a flexible second component;
a pusher; and,
a restraining element releasably restraining said flexible second component to said catheter;
wherein said second component is self-expanding and associated with said first component such that said second component can be distally inverted over said first component.

10. The obstruction removal device of claim 9 further comprising: a delivery device slidably containing at least said first component.

11. The obstruction removal device of claim 9 wherein said second component has a distal end fixed to a distal end of said catheter.

12. The obstruction removal device of claim 9 wherein said second component comprises a mesh.

* * * * *